(12) United States Patent
Erpen

(10) Patent No.: US 10,300,250 B2
(45) Date of Patent: May 28, 2019

(54) DEVICE FOR THE TREATMENT OF VARICOSE VEINS

(71) Applicant: Gefässpraxis Dr. Erpen AG, Visp (CH)

(72) Inventor: Thomas Erpen, Visp (CH)

(73) Assignee: GEFASSPRAXIS DR. ERPEN AG, Visp (CH)

(*) Notice: Subject to any disclaimer, the term of this patent is extended or adjusted under 35 U.S.C. 154(b) by 91 days.

(21) Appl. No.: 15/252,320

(22) Filed: Aug. 31, 2016

(65) Prior Publication Data

US 2017/0056048 A1 Mar. 2, 2017

(30) Foreign Application Priority Data

Aug. 31, 2015 (EP) .................................... 15183162

(51) Int. Cl.
*A61M 25/10* (2013.01)
*A61M 25/00* (2006.01)
(Continued)

(52) U.S. Cl.
CPC ........ *A61M 25/10* (2013.01); *A61B 17/00008* (2013.01); *A61B 17/22* (2013.01); *A61B 17/32* (2013.01); *A61B 17/320016* (2013.01); *A61B 17/320725* (2013.01); *A61M 25/007* (2013.01); *A61B 17/00491* (2013.01);
(Continued)

(58) Field of Classification Search
CPC .. A61M 2025/0004; A61M 2025/0008; A61M 25/007; A61M 2025/0096; A61M 25/10; A61M 2025/1086; A61M 2025/109; A61B 17/00008; A61B 17/22; A61B 17/32; A61B 17/320016; A61B 17/3205; A61B 17/320725; A61B 17/3209; A61B 2017/00778; A61B 2017/00893; A61B 2017/22051; A61B 2017/22082; A61B 2017/320004; A61B 2017/320008; A61B 2017/32006; A61B 2017/320741
See application file for complete search history.

(56) References Cited

U.S. PATENT DOCUMENTS 5,282,484 A * 2/1994 Reger ............... A61B 17/32075
128/898
5,908,407 A * 6/1999 Frazee ............... A61M 25/1011
604/101.01
(Continued)

FOREIGN PATENT DOCUMENTS

EP 1169970 1/2002
EP 1997443 12/2008
(Continued)

OTHER PUBLICATIONS

European Search Report EP15183162 dated Feb. 8, 2016.

*Primary Examiner* — Shefali D Patel
(74) *Attorney, Agent, or Firm* — Young & Thompson

(57) ABSTRACT

A device for treatment of varicose veins includes a catheter (1), which can be inserted into a vein to be treated. There is a balloon (2) with at least one cutting element (3) for cutting at least part of an inner wall of the vein arranged on a proximal end (1a) of the catheter. The catheter has side openings (7a-7c), through which a sclerosing agent can be introduced into the vein. The at least one cutting element includes a cutting edge configured to cut intima and media of the vein when withdrawing the balloon from the vein after treatment with the sclerosing agent.

25 Claims, 3 Drawing Sheets

(51) Int. Cl.
*A61B 17/32* (2006.01)
*A61B 17/00* (2006.01)
*A61B 17/3207* (2006.01)
*A61B 17/22* (2006.01)
*A61M 31/00* (2006.01)

(52) U.S. Cl.
CPC ........... *A61B 2017/00778* (2013.01); *A61B 2017/00893* (2013.01); *A61B 2017/22051* (2013.01); *A61B 2017/22065* (2013.01); *A61B 2017/320004* (2013.01); *A61B 2017/32006* (2013.01); *A61B 2017/320008* (2013.01); *A61B 2017/320741* (2013.01); *A61M 25/0082* (2013.01); *A61M 31/00* (2013.01); *A61M 2025/0096* (2013.01); *A61M 2025/109* (2013.01); *A61M 2025/1086* (2013.01); *A61M 2202/0468* (2013.01); *A61M 2210/12* (2013.01)

(56) References Cited

U.S. PATENT DOCUMENTS

| | | | |
|---|---|---|---|
| 5,916,193 A * | 6/1999 | Stevens | A61M 1/3659 604/28 |
| 6,726,677 B1 | 4/2004 | Flaherty et al. | |
| 8,377,083 B2 * | 2/2013 | Mauch | A61B 17/320725 128/898 |
| 2002/0029015 A1 * | 3/2002 | Camenzind | A61B 17/22 604/97.02 |
| 2003/0120256 A1 | 6/2003 | Lary et al. | |
| 2004/0158143 A1 | 8/2004 | Flaherty et al. | |
| 2005/0055040 A1 | 3/2005 | Tal | |
| 2006/0149218 A1 * | 7/2006 | Slater | A61M 25/00 604/509 |
| 2007/0282359 A1 | 12/2007 | Tal | |
| 2008/0300594 A1 | 12/2008 | Goto | |
| 2011/0046543 A1 | 2/2011 | Brandeis | |
| 2011/0218494 A1 | 9/2011 | Gerrans et al. | |
| 2012/0259216 A1 | 10/2012 | Gerrans et al. | |
| 2013/0030410 A1 * | 1/2013 | Drasler | A61B 18/04 604/510 |

FOREIGN PATENT DOCUMENTS

| | | |
|---|---|---|
| EP | 2508223 | 10/2012 |
| WO | 2004112569 | 12/2004 |
| WO | 2009109967 | 9/2009 |
| WO | 2013090563 | 6/2013 |
| WO | 2015052703 | 4/2015 |

* cited by examiner

DEVICE FOR THE TREATMENT OF VARICOSE VEINS

CROSS-REFERENCE TO RELATED APPLICATIONS

This application claims foreign priority to foreign application EP 15183162, filed Aug. 31, 2015 in the European Patent Office.

FIELD OF THE INVENTION

The invention concerns a device for the treatment of varicose veins.

BACKGROUND OF THE INVENTION

Alongside surgical procedures and sclerotherapy, endovenous procedures (laser, radio frequency, ClariVein®) have increasingly become more important in the treatment of varicose veins in recent years. These procedures reveal themselves to be efficient for the ablation of saphenous veins and to have fewer side effects for the patients than conventional surgical procedures. However, laser, radio frequency as well as ClariVein® require relatively expensive equipment. Alongside the catheters, devices for producing the laser or the radio frequency waves are required. For ClariVein® (cf. e.g. WO 2013/090563 A1), a quickly rotating wire with a specially angled tip within the catheter which strikes against the inner wall of the vessel causes a vessel spasm. At the same time, a liquid sclerosing agent, polidocanol, is injected. The quickly rotating tip also causes swirling of the sclerosing agent and thus brings it evenly into contact with the entire inner wall of the vein and sclerotizes it.

All in all, the known endovenous procedures use expensive devices which make the treatment expensive.

SUMMARY OF THE INVENTION

Therefore, the problem addressed by the present invention is to provide for a device with a simpler design which allows for the effective treatment of varicose veins.

A device which solves this problem comprises a catheter, which has a balloon with at least one cutting element ("cutting balloon") and which has side openings. A sclerosing agent can get into the vein through these. Using the "cutting balloon," at least part of the inner wall of the vein can be cut in order to bring about the destruction of the intima and media of the vein. The device thus allows for treatment in the form of endovenous chemomechanical catheter ablation. As a result of the combination of sclerotherapy with mechanical destruction of the insufficient veins, the effectiveness of the treatment can be increased in comparison with sclerotherapy alone. In comparison with conventional endovenous procedures, no additional use of expensive supplementary equipment is required. All in all, the design of the device according to the invention is relatively simple and the equipment requirements can be reduced, wherein a treatment which is efficient as well as time and cost-effective is made possible.

BRIEF DESCRIPTION OF THE DRAWINGS

Other specific design features of the device and their benefits can be seen from the following description and illustrations of embodiments. In the following, the directional terms "proximal" and "distal" refer to these directions relative to the human body, in which the device for the treatment of varicose veins is used.

In the drawings.

DETAILED DESCRIPTION OF THE PREFERRED EMBODIMENTS

First Embodiment

Figure 1:
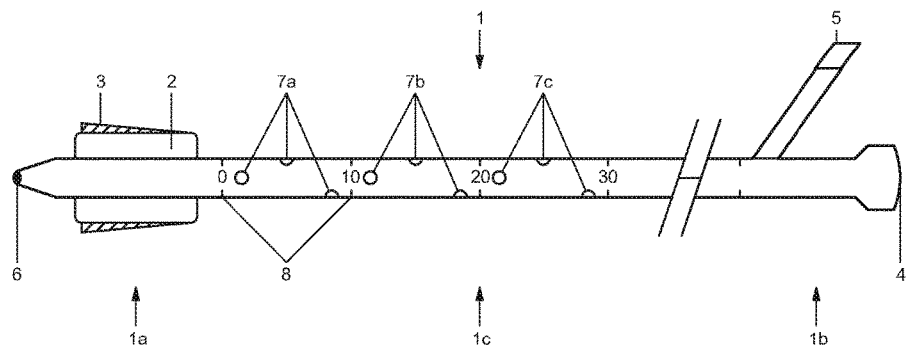
FIG. 1 shows a first embodiment of the outer catheter of a device for the treatment of varicose veins in a partly sectional side view.

FIG. 1 shows a first catheter 1 (hereinafter also referred to as the "outer catheter") which is used as a device for the endovenous treatment of varicose veins and which can be inserted into a vein. The catheter 1 has a proximal end section 1a with a balloon 2 which is shown in a sectional view in FIG. 1 and in an expanded state and which carries cutting elements 3, and a distal end section 1b with an intake opening 4 and a connection 5 which has a fluid connection to the balloon 2 via a subchannel 1e ("lumen") (cf. FIG. 5). A syringe or similar can be connected at connection 5 in order to pump a fluid into balloon 2 via the subchannel 1e or to drain it again, and thus to allow for the inflation and deflation of the balloon 2. In order to avoid endangering a patient as a result of any possible leakage from the balloon 2 inserted into the vein, air is not be used as the fluid for inflation. Instead, a liquid such as a sodium chloride solution is used. The proximal end section 1a includes a tapering end which is fitted with a through-going end opening 6. The latter has a fluid connection with the intake opening 4 via a main channel 1d ("lumen") (cf. FIG. 5).

The catheter 1 is fenestrated. For this purpose, it has an intermediate section 1c between the two end sections 1a and 1b which is equipped with side openings 7a-7c ("catheter windows"). These are distributed around the circumference of catheter 1 and have a fluid connection with intake opening 4 via the main channel 1d. During use, a sclerosing agent can be injected into the vein to be treated via the side openings 7a-7c. Two neighboring side openings 7a-7c are arranged offset axially and radially from one another. The offset allows for a more homogeneous distribution of sclerosing agent in the vein.

Along the intermediate section 1c, there are markings 8 on the catheter shaft which are placed at regular intervals for instance and, among other things, provide information about how far the catheter 1 has been inserted into the vein. In the variant according to FIG. 1, the markings 8 can be seen in the form of lines and numbers 0, 10, 20, 30. Other types of markings are possible, of course.

The side openings 7a-7c are arranged in groups so that the intermediate section 1c is divided into sections which each have the same arrangement of side openings 7a-7c. In the variant according to FIG. 1, for example, a group with three side openings 7a can be seen between the 0 to 10 section. The same arrangement of side openings is repeated in the 10 to 20 section and in the 20 to 30 section. The side openings 7a, 7b, 7c of the same group are arranged radially offset at an angle. In an example with three side openings, this angle can be 120 degrees. However, an uneven radial distribution is also possible. Furthermore, the number of side openings 7a-7c per group, i.e. per section can be different from that shown in FIG. 1 and can be one, two or more. Since the side openings 7a-7c reach through the outer wall of the catheter 1, the number and arrangement are chosen so that sufficient space remains to be able to provide at least one closed subchannel from connection 5 to balloon 2 (cf. subchannel 1e in FIG. 5).

Figure 2:
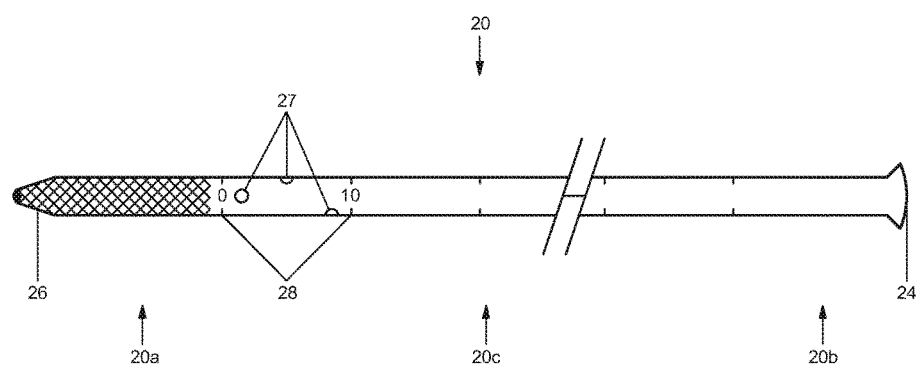
FIG. 2 shows a side view of an inner catheter which can be accommodated in the outer catheter according to FIG. 1.

A second catheter 20 (hereinafter also referred to as the "inner catheter") can be inserted via the intake opening 4 in the outer catheter 1, as shown in FIG. 2. The catheter 20 has a proximal end section 20a and a distal end section 20b with a connection 24. The proximal end section 20a is formed by a closed wall. In particular, in contrast to the outer catheter 1, the tapering end 26 does not have an end opening. The closed end 26 of the inner catheter 20 allows the lumen at the tip of the outer catheter 1 to be closed, wherein a backflow to the proximal is prevented when using a sclerosing agent.

Between the two end sections 20a and 20b, the catheter 20 has an intermediate section 20c which has an inner channel ("lumen") and which is provided with side openings 27. The latter have a fluid connection to connection 24 via the inner channel. As can be seen in FIG. 2, the catheter 20 is only provided with side openings 27 on one section adjacent to the proximal end section 20a, while the rest of the catheter shaft does not have any openings. In contrast to the outer catheter 1, therefore, only one group of side openings 27 is provided. Preferably, the number and/or arrangement of the side openings 27 matches the number and/or arrangement of the first group of side openings 7a on the outer catheter 1. In the example according to FIG. 2, three side openings 27 can be seen which are arranged radially and axially offset from one another similar to the side openings 7a in FIG. 1. Depending on the design, the number of side openings 27 can be one, two or more.

Along the intermediate section 20c, there are markings 28 on the catheter 20 which are placed at regular intervals for instance and, among other things, provide information about how far the catheter 20 has been inserted into the outer catheter 1. Lines, numbers, etc. are used for instance as markings 28.

During use, the inner catheter 20 is inserted into the outer catheter 1 and is then withdrawn section by section. As a result, the side openings 27 are first located near the side openings 7a, then near the side openings 7b, etc. Thereby, the closed end section 20a of the inner catheter 20 seals the main channel 1d in the outer catheter 1 between the ends 6 and 26. A sclerosing agent can thus be introduced into the vein to be treated section by section via the connection 24 and the side openings 27 and 7a-7c.

Figure 3:
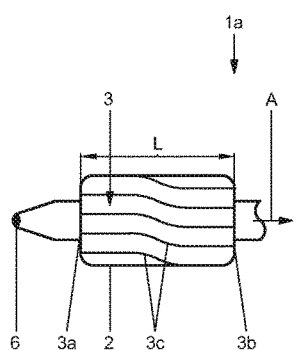
FIG. 3 shows the proximal end section of the outer catheter according to FIG. 1 in a plan view.
Figure 4:
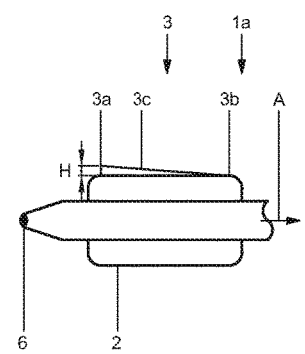
FIG. 4 shows the proximal end section according to FIG. 3 in longitudinal section so that a cutting element can be seen from the side.

FIGS. 3 and 4 show the design of the proximal end section 1a of the outer catheter 1 in detail, wherein the balloon 2 is shown in an expanded state. The direction in which the axis A runs, along which the outer catheter 1 stretches from end section 1a to end section 1b, is hereinafter referred to as "axial," while "radial" is transverse to the axis A.

The balloon 2 is a "cutting balloon" and, to this end, has one or more cutting elements 3 ("blades"). FIG. 3 shows multiple cutting elements 3 which extend parallel to one another in an axial direction and which are arranged around the balloon 2. As is apparent, each cutting element 3 does not run straight as seen in the axial direction A, but rather its cutting edge 3c shows a curved path at least along a section.

A wide variety of path forms are possible. For example, the cutting edge 3c can be curved so that it winds around the axis A, e.g. in a spiral. It is also possible that, viewed in the direction of the axis A, the cutting edge 2a has a section with a straight axial path which segues into another straight section via a curved intermediate section. It is also possible to design just a single cutting element 3 which runs around the axis A.

The uneven path of a cutting element 3 has the result that, viewed in the axial direction A, the ends 3a and 3b of a cutting element 3 are arranged radially offset at an angle which is greater than 0 degrees. Preferably, the angle is at least 10 degrees, and an angle of at least 20 degrees is particularly preferred. Furthermore, the path can be designed so that the aforesaid angle is smaller than 360 degrees. Preferably, the angle is at most 180 degrees, and an angle of at most 90 degrees is particularly preferred.

As can be seen in FIG. 4, the shape of a cutting element 3 also changes transverse to the axis A, in that the cutting edge 3c runs at a height which decreases in the direction towards the distal end section 1b. The distal end 3b of the cutting element 3 is therefore located closer to the center of the axis A than the proximal end 3a. In the present embodiment, the cutting element 3 is wedge-shaped. The maximum height H of a cutting element 3 is typically in a range of 0.5 to 1.5 mm.

The balloon 2 extends axially along a length L which is typically in the range of 5 to 30 mm.

The axially and/or radially variable shape of a cutting element 3 allows for a comprehensive mechanical effect on the inner wall of the vein when the catheter 1, inserted into the vein, is withdrawn again. In doing so, the tapering cutting edges 3c gradually dig into the inner wall of the vein like a plough. An abrupt mechanical effect is thus avoided so that a less painful treatment is possible which, in some circumstances, can even be carried out without local anesthetic in the form of a tumescent anesthetic. This is the case, for example, if Aethoxysklerol® is used as a sclerosing agent since this is also a local anesthetic.

Figure 5:
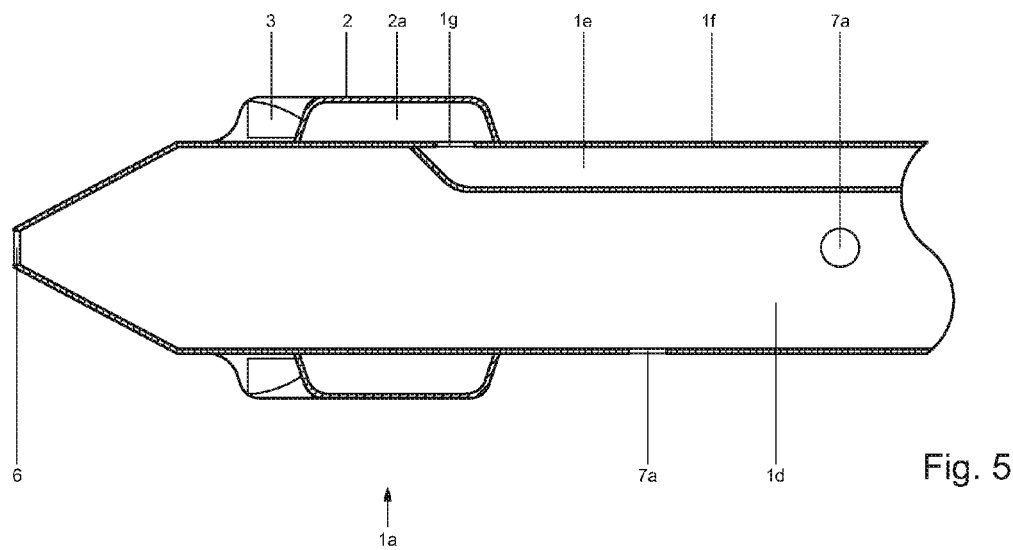
FIG. 5 shows the proximal end section of the outer catheter according to FIG. 1 in a partly sectional side view.

FIG. 5 shows the proximal end section 1a of the outer catheter 1 in a partly sectional longitudinal view, wherein the balloon 2 is shown in a non-inflated state. The catheter 1 has an outer wall 1f which defines the main channel 1d. The inner catheter 20 can be inserted into this channel 1d during the treatment. When required, a wire which is inserted into the vein beforehand and along which the outer catheter 1 is pushed so that the wire runs through the end opening 6, the main channel 1d and the intake opening 4 is used as a guide.

The balloon 2 is formed of an envelope which runs around the outer wall 1f and which encloses a compartment 2a. The latter is connected to the subchannel 1e, which leads to the intake opening 4, via at least one passage opening 1g formed in the outer wall 1f. The cutting elements 3 are attached to the envelope 2. The envelope of the balloon 2 is folded together in a non-inflated state so that it shows the smallest possible spread in a radial direction.

Second Embodiment

Figure 6:
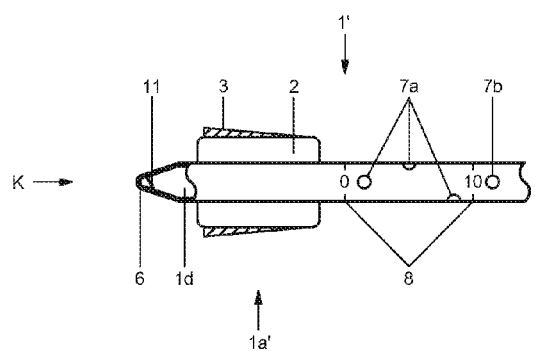
FIG. 6 shows a second embodiment of the outer catheter of a device in a partly sectional side view.
Figure 7:
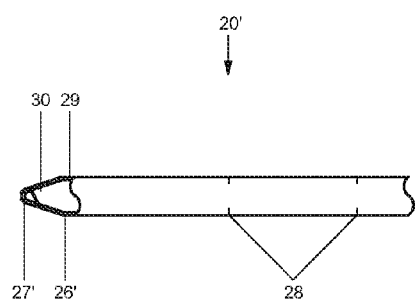
FIG. 7 shows a partly sectional side view of an inner catheter which can be accommodated in the outer catheter according to FIG. 6.

The device with the catheters 1 and 20 according to FIGS. 1 and 2 is particularly suitable for the treatment of large veins, e.g. saphenous veins. FIGS. 6 and 7 show another embodiment of the device with catheters 1', 20' which is particularly suitable for use in smaller veins, e.g. side branches.

FIG. 6 shows a part of the outer catheter 1' which has the same elements 2-8 as the outer catheter 1 according to FIG. 1. Unlike the latter, there is also a one-way valve 11, e.g. in the form of a non-return valve, arranged at the proximal end section 1a' in the main channel 1d. The one-way valve 11 is used to close the end opening 6 so that this is passable in the caudal direction, i.e. from outside into the main channel 1d (cf. arrow K in FIG. 6), but not in the opposite direction. Thus, a wire, for example, which has been inserted into the vein to be treated as a guide can be inserted into the main channel 1d of the outer catheter 1' in the direction K via the intake opening 6, whereas the sclerosing agent which is in the main channel 1d cannot get out through the end opening 6.

FIG. 7 shows the inner catheter 20', wherein the distal end section 20b with the connection 24 corresponds to that of the inner catheter 20 according to FIG. 2. Unlike the latter, the inner catheter 20' does not have any side opening 27. The outer wall 29, which encloses the channel 30 leading to the connection 24, is thus established in a closed form. The proximal end 26' of the inner catheter 20' ends in a through-going discharge opening 27'.

If the inner catheter 20' is inserted into the outer catheter 1' then the sclerosing agent can be introduced into the main channel 30 via the connection 24, from where it can then get into the vein to be treated through the discharge opening 27' and through the side openings 7a-7c in the outer catheter 1'. As in the first embodiment, a vein can be treated in sections by switching between injecting sclerosing agent and withdrawing the inner catheter 20' by one section. As a result, the discharge opening 27' moves into the vicinity of the side openings 7a, 7b, 7c, etc.

Common materials which can be sterilized can be used to manufacture the catheters 1, 1, 20, 20'. The walls which define the channels in the catheters 1, 1, 20, 20' can be made from plastic, for example, so that a flexible tube can be designed. Preferably, the catheters 1, 20 and 1', 20' are designed to be single-use and are provided in a sterile form in packaging.

Applications:

A possible application of the device with the catheters 1 and 20 is explained in more detail below on the basis of FIGS. 8 to 10.

Figure 8:
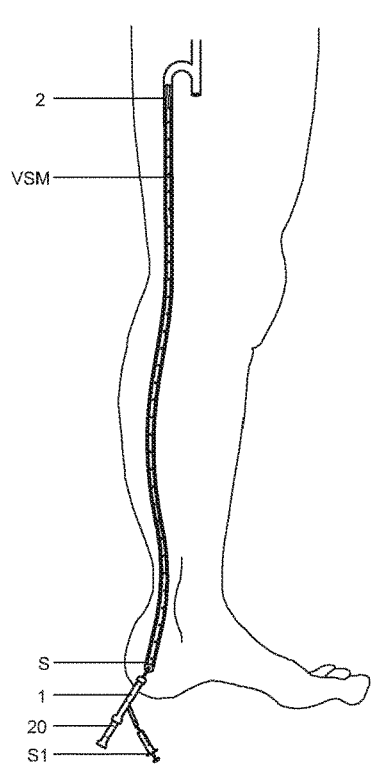
FIG. 8 shows schematically a leg with the saphenous vein into which the catheters of FIGS. 1 and 2 are inserted.

FIG. 8 shows a leg with the vena saphena magna VSM and an access port S which was inserted into the vein using the Sedlinger technique.

1st Step

The catheter 1 is inserted through the access port S, advanced through the saphenous vein VSM under ultrasound monitoring and the tip is placed 1.5 cm caudal to the saphenofemoral junction. The balloon 2 is then inflated using a syringe 51 connected to the connection 5. It remains so during the entire sclerosing phase (2nd step).

If direct advancement of the catheter 1 is difficult, a wire (not shown in FIG. 8 to 10) can be inserted into the vein VSM in advance as a guide and the catheter 1 can then be inserted via the wire.

Any dissection during insertion of the catheter 1 and/or of the wire is unproblematic since the vein will be destroyed anyway.

After placement of the outer catheter 1, the wire, where applicable, is removed and the inner catheter 20 is inserted into the main channel 1d. If no wire is used then the inner catheter 20 can already have been inserted into the outer catheter 1 so that both catheters 1, 20 can be inserted into the vein together.

2nd Step

The sclerosing is performed. The sclerosing agent is fed in (preferably as foam, e.g. Aethoxysklerol® 1% or another agent containing polidocanol) through the inner catheter 20 using a syringe S2 connected to the connection 24. The inner catheter 20 is withdrawn in 10 cm sections. 1 ml of Aethoxysklerol® 1% is applied as foam for each 10 cm and you should wait approx. 1 minute. This process is repeated until the entirety of the inner catheter 20 has been removed.

Figure 9:
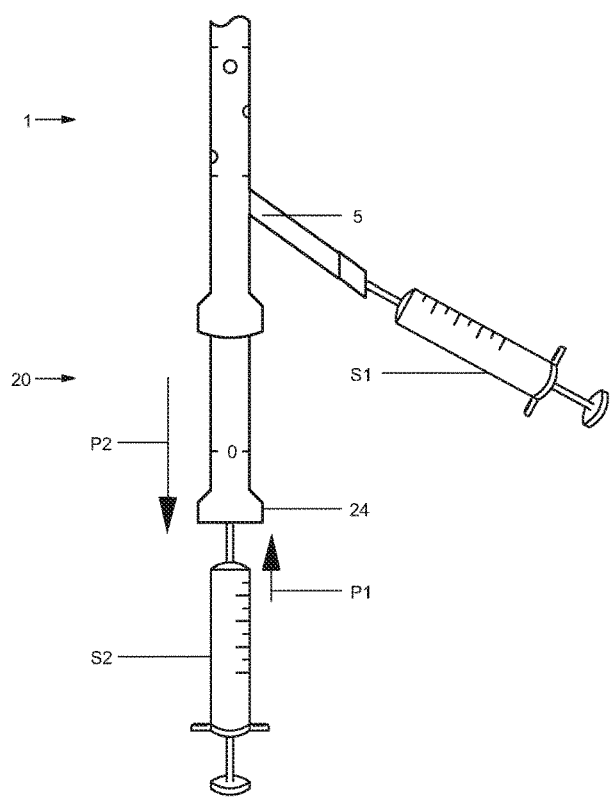
FIG. 9 shows the distal end of the combined catheters of FIGS. 1 and 2 with attached syringes.

In FIG. 9, the application is indicated by the arrow P1 and the withdrawal of the inner catheter 20 is indicated by the arrow P2.

Figure 10:
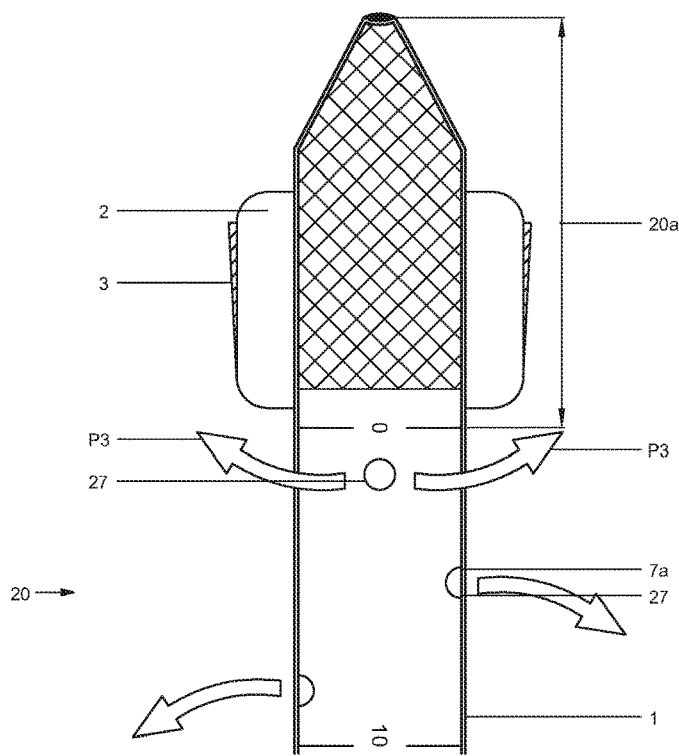
FIG. 10 shows the proximal end of the combined catheters of FIGS. 1 and 2, wherein the outer catheter is shown in section.

In FIG. 10, in which the outer catheter 1 is shown in section and the inner catheter 20 is inserted fully into it, the emission of the sclerosing agent out of the side openings 27 and 7a is indicated by the arrows P3. As explained above, the lumen of the inner catheter 20 has a closed design at the proximal end. This closed area, which reaches to the 0 mark for example, is indicated in FIG. 10 by the double arrow at 20a

3rd Step

The effect of the sclerosing agent has caused a vasospasm. In addition, the sensitivity to pain should be reduced. The balloon 2 is deflated for approx. 20 seconds and is then inflated again. The vein VSM can thus "drain" itself. The catheter 1 with the inflated balloon 2 is now slowly withdrawn (approx. 3 seconds per 10 cm). The resistance should be readily detectable during withdrawal, however "ripping out" should be avoided. The intima and media of the vein are destroyed by the mechanical effect of a cutting element 3 on the balloon 2. The special shape of a cutting element 3 allows for the effective destruction of the inner wall of the vein, which is cut into multiple fragments when the balloon 2 is withdrawn.

The device according to the second embodiment can be used in an analogous manner as set out above. Here, the inner catheter 20' can already be inserted into the outer catheter 1' from the beginning even if a wire is used since the wire can run through the end openings 6, 27' and the one-way valve 11 in the inside of the catheter 20' while the catheters 1', 20' are inserted into the vein.

A wide variety of modifications are available to the person skilled in the art from the description above without leaving the scope of protection for the invention which is defined by the claims.

In a simpler embodiment, for example, it is possible to leave the inner catheters 20, 20' out and simply design a catheter with a "cutting balloon" 2, 3 and the side openings 7a-7c.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A device for treatment of varicose veins, comprising:
an outer catheter, which is insertable into a vein to be treated, the outer catheter extending lengthwise in an axial direction,
a balloon arranged on a proximal end of the outer catheter,
at least one cutting element for cutting at least part of an inner wall of the vein arranged on the balloon on the outer catheter, wherein the outer catheter comprises side openings, through which a sclerosing agent can be introduced into the vein, and
wherein the at least one cutting element includes a cutting edge that is elongated along the axial direction of the outer catheter, a length of the cutting edge along the axial direction of the outer catheter being greater than a width of the cutting edge, the cutting edge being configured to cut intima and media of the vein in order that a mechanical effect of the at least one cutting element destroys the intima and the media of the vein when withdrawing the balloon from the vein after treatment with the sclerosing agent.

2. The device according to claim 1,
wherein said cutting edge has, at least in an inflated state of the balloon, a shape, which changes in at least one of the axial direction and a radial direction of the outer catheter, and
wherein in the inflated state, a maximum height of the at least one cutting element in the radial direction is in a range of 0.5 mm to 1.5 mm.

3. The device according to claim 1, wherein the at least one cutting element comprises a distal end, a proximal end, and at least one curved portion extending between the distal and proximal ends in the axial direction along an axial section of the outer catheter, the distal end of the at least one cutting element, viewed in the axial direction, is arranged radially offset at an angle which is greater than 0 degrees from the proximal end of the at least one cutting element.

4. The device according to claim 1, wherein two of the side openings are arranged adjacent each other and offset from one another in at least one of the axial direction and a radial direction.

5. The device according to claim 1, wherein the outer catheter is divided into sections, which each have a same number of the side openings or a same arrangement of the side openings or both.

6. The device according to claim 1, wherein the outer catheter comprises at least one subchannel, which is arranged radially offset from a main channel and which provides a fluid connection between the balloon and an access.

7. The device according to claim 1, wherein the proximal end of the outer catheter comprises an end opening.

8. The device according to claim 1, wherein the outer catheter comprises a one-way valve at the proximal end.

9. The device according to claim 1, further comprising an inner catheter insertable at least partly within the outer catheter.

10. The device according to claim 9, wherein the inner catheter comprises an access for introduction of the sclerosing agent and at least one opening, through which the sclerosing agent can be conducted to the side openings on the outer catheter.

11. The device according to claim 9, wherein the inner catheter comprises a closed proximal end and adjacent thereto a portion with at least one side opening.

12. The device according to claim 11, wherein a part of the inner catheter after said portion to a distal end of the inner catheter is free of any side openings after said portion to the distal end.

13. The device according to claim 9, wherein the inner catheter comprises a number of side openings, which is smaller than a number of the side openings on the outer catheter.

14. The device according to claim 13, wherein the number of the side openings on the inner catheter matches with a number of the side openings on a section of the outer catheter.

15. The device according to claim 14, wherein an arrangement of the side openings on the inner catheter matches with an arrangement of the side openings on the section of the outer catheter.

16. The device according to claim 9, wherein the inner catheter comprises a proximal end with an end opening.

17. The device according to claim 16, wherein the inner catheter is free of any side openings from the proximal end of the inner catheter to a distal end of the inner catheter.

18. The device according to claim 9, wherein the inner catheter comprises markings for indicating a length.

19. The device according to claim 1, wherein the outer catheter comprises markings for indicating a length.

20. The device according to claim 19, wherein the markings are arranged at regular intervals.

21. The device according to claim 1, wherein the side openings are arranged between the balloon and a distal end of the outer catheter.

22. A device for treatment of varicose veins, comprising:
an outer catheter, which is insertable into a vein to be treated, the outer catheter extending lengthwise in an axial direction,
a balloon arranged on a proximal end of the outer catheter,
at least one cutting element for cutting at least part of an inner wall of the vein arranged on the balloon on the outer catheter,
wherein the outer catheter comprises side openings, through which a sclerosing agent can be introduced into the vein, and
wherein the at least one cutting element includes a cutting edge that is elongated along the axial direction of the outer catheter, a length of the cutting edge along the axial direction of the outer catheter being greater than a width of the cutting edge, the cutting edge being configured to cut intima and media of the vein in order that a mechanical effect of the at least one cutting element destroys the intima and the media of the vein when withdrawing the balloon from the vein after treatment with the sclerosing agent,
wherein the at least one cutting element has a maximum height nearest a forward-most proximal portion of the at least one cutting element, and a height which decreases from the forward-most proximal portion to a rearmost distal portion of the at least one cutting element towards a distal end of the outer catheter.

23. A device for treatment of varicose veins, comprising:
an outer catheter, which is insertable into a vein to be treated, the outer catheter extending lengthwise in an axial direction,
a balloon arranged on a proximal end of the outer catheter,
at least one cutting element for cutting at least part of an inner wall of the vein arranged on the balloon on the outer catheter, wherein the outer catheter comprises side openings, through which a sclerosing agent can be introduced into the vein, and wherein the at least one cutting element includes a cutting edge that is elongated along the axial direction of the outer catheter, a length of the cutting edge along the axial direction of the outer catheter being greater than a width of the cutting edge, the cutting edge being configured to cut intima and media of the vein in order that a mechanical effect of the at least one cutting element destroys the intima and the media of the vein when withdrawing the balloon from the vein after treatment with the sclerosing agent, wherein the at least one cutting element has a proximal, first end, a curved intermediate section which segues the first end into a distal, second end, the first and second ends being arranged radially offset at a non-zero angle when viewed in the axial direction in which the outer catheter extends.

24. The device according to claim 23, wherein said angle is at least 10 degrees.

25. The device according to claim 23, wherein said angle is at least 20 degrees.

* * * * *